United States Patent [19]

Robbins et al.

[11] Patent Number: 4,731,201

[45] Date of Patent: Mar. 15, 1988

[54] SHAMPOO METHOD AND COMPOSITION

[75] Inventors: Clarence Robbins, Piscataway; Charles Reich, Highland Park, both of N.J.

[73] Assignee: Colgate-Palmolive Company, New York, N.Y.

[21] Appl. No.: 895,764

[22] Filed: Aug. 12, 1986

[51] Int. Cl.$^4$ .............................................. C11D 1/29
[52] U.S. Cl. ................................... 252/551; 252/546; 252/547; 252/553; 252/555; 252/DIG. 13; 252/DIG. 14
[58] Field of Search ............... 252/551, 553, 555, 546, 252/547, DIG. 13; 558/34

[56] References Cited

U.S. PATENT DOCUMENTS

| | | | |
|---|---|---|---|
| 3,391,750 | 7/1968 | Zika | 175/71 |
| 3,501,409 | 3/1970 | Matson et al. | 252/551 |
| 3,775,349 | 11/1973 | Tuvell et al. | 252/551 |
| 4,024,078 | 5/1977 | Gilbert et al. | 252/551 |
| 4,075,129 | 2/1978 | Murata et al. | 252/527 |
| 4,166,048 | 8/1979 | Nishimura et al. | 252/546 |
| 4,549,984 | 10/1985 | Satsuki et al. | 252/532 |
| 4,554,098 | 11/1985 | Klisch et al. | 252/547 |
| 4,555,360 | 11/1985 | Bissett | 252/541 |
| 4,608,197 | 8/1986 | Kesling et al. | 252/551 |

FOREIGN PATENT DOCUMENTS 1170420 1/1959 France .
1281895 7/1972 United Kingdom .

*Primary Examiner*—Prince E. Willis
*Attorney, Agent, or Firm*—Richard N. Miller; Richard J. Ancel; Herbert S. Sylvester

[57] ABSTRACT

This invention relates to a method of removing mono-$C_{12}$-$C_{18}$ alkyl quaternary ammonium hair conditioners from the hair by washing said hair with a cleaning composition containing a $C_6$-$C_{10}$ alketh (1-5) sulfate salt as the principal detergent and to cleaning compositions for use in the inventive method.

25 Claims, No Drawings

SHAMPOO METHOD AND COMPOSITION

BACKGROUND OF THE INVENTION AND PRIOR ART

In this specification, the words deceth (1-5) sulfate, laureth (0-5) sulfate, etc., are used to describe the neutralized salt of the sulfuric half ester of the reaction product of decanol, lauryl alcohol, etc., with an average of 1-5 or 0-5 moles of ethylene oxide. The words decyl monoethoxy sulfate and lauryl diethoxy sulfate are used to describe the essentially pure compounds.

Hair conditioning compositions are often used after shampooing in order to make the hair more manageable and to facilitate both wet combing and dry combing. While a great variety of ingredients have been used for the purpose of conditioning, cationic surfactants are among the most generally used materials, with the mono-$C_{12}$-$C_{18}$ alkyl quaternary ammonium salts being found in most of the popular hair conditioning products.

Typically, the conditioning compositions which utilize the mono-$C_{12}$-$C_{18}$ alkyl quaternary conditioner contain from 1% to 6% by weight of the quaternary conditioner. This conditioner is effective because it is adsorbed by the hair. However, as some interaction occurs between the hair and the mono-alkyl quaternary ammonium conditioner, it has been noted that often not all of the conditioner is removed when the hair is subsequently shampooed. The build up of conditioner causes the hair to appear dull, i.e., not shiny and can also lead to hair that is limp and less manageable. More specifically, it has been discovered that shampoos containing lauryl sulfate and/or laureth (1-5) sulfate detergents—the primary detergent ingredients in most shampoos—do not copletely remove the mono-$C_{18}$ alkyl quaternary ammonium conditioners from the hair. Additionally, it has been discovered that lauryl and/or laureth (1-5) sulfate detergents combine with the mono-$C_{12}$-$C_{18}$ quaternary ammonium conditioners to form a water-insoluble complex that can build up on the hair with repeated shampoo and conditioner applications. Furthermore, no patents on the shampoos were noted in which the chain length of the alkyl group on the anionic alkyl sulfate and alketh (1-5) sulfate detergents averaged less than 12 carbon atoms.

In reviewing the patent literature for alternatives to shampoos containing a lauryl sulfate or a laureth (1-5) sulfate salt as the principal detergent, U.S. Pat. No. 3,775,349 was noted. This patent confirms that the optimum chain length for the anionic alketh (0-5) sulfate detergents is twelve carbons and that a typical distribution for such detergents which are based upon mid-cut coconut alcohols is 2% decyl, 66% dedecyl, 23% tetradecyl and 9% hexadecyl sulfate. The invention described in U.S. Pat. No. 3,775,349 is based upon the discovery that the foaming performance in dishwashing of $C_{10}$-$C_{16}$ alketh (0-6) sulfates in hard water is improved when used in conjunction with a lauryl dimethyl amine oxide foam booster (5 detergent:1 amine oxide) at 0.45% concentration if from 10% to 50%, preferably 15% to 40%, by weight of deceth (3) sulfate is present in the formulation. In soft water, the presence of deceth (3) sulfate offers no advantage when present in amounts up to 35% by weight, but thereafter foaming performance is adversely affected, falling to 50% of the standard dishwashing formulation when 63% by weight of deceth (3) sulfates are present. Since the foaming performance of the inventive compositions was from 70% to 89% of the performance of a standard dishwashing detergent, this patent teaches away from the use of alketh (1-5) sulfate detergents containing more than 40% by weight of the corresponding deceth (3) sulfates.

Another patent noted was U.S. Pat. No. 4,024,078 which discloses liquid detergent compositions that are effective in cleaning dried on food soils from dishes and contain from 10% to 80%, preferably 15% to 60%, by weight of a mixture of decyl ethoxy and isopropoxy sulfates wherein at least 20% of said sulfates are monoalkoxylated. Table II of this patent purports to show that decyl monoethoxy sulfate is superior in cleaning to the di-, tri,- tetra- and non-ethoxy sulfates of decyl alcohol when used in a formula containing, by weight, 25% of alkyl sulfate, 4% of sodium coconut glyceryl ether sulfonate, 5% coconut dimethyl amine oxide and the balance water, but the standard deviation of 0.6 for the cleaning scores shows that there is no significant difference in any of the cleaning scores presented. The indicated cleaning values show that decyl monoethoxy sulfate was equivalent in performance to dodecyl sulfate and tridecyl sulfate and inferior in performance to undecyl sulfate. Furthermore, the cleaning scores presented suggest that a mixture of dodecyl polyethoxy sulfates containing equal parts of 0, 1, 2, 3 and 4 ethenoxy groups would exhibit better cleaning performance than the same mixture of decyl polyethoxy sulfates. Thus, Table II suggests that the disclosed formulation containing pure decyl monoethoxy sulfate will be superior in cleaning to the same formula containing, for example, dodecyl monoethoxy sulfate or decyl diethoxy sulfate.

Table IV of the patent shows that the formulation in Table II containing decyl monoethoxy sulfate exhibits poorer sudsing in both hard and soft water than the same formulation containing dodecyl monoethoxy sulfate and that various mixtures of 10-30% decyl monoethoxy sulfate and 90-70% dodecyl monoethoxy sulfate in said formulation exhilitabout the same sudsing performance as the dodecyl monoethoxy sulfate. Additionally, Table III shows that the same formulation containing decyl triethoxy sulfate exhibits poorer foaming than said formulation containing dodecyl triethoxy sulfate. Thus, this patent teaches that a liquid formulation containing decyl monoethoxy sulfate is effective in removing a mixture of white milk and French's gravy from glasses and that the same formulation containing a mixture of 10-30% by weight of deceth (1-3) sulfate and 90-70% of dodeceth (1-3) sulfate is comparable in cleaning and sudsing to dodecyl triethoxy sulfate.

In view of the teachings of U.S. Pat. Nos. 4,024,078 and 3,775,349 it was surprising to discover that a hair cleaning composition containing a $C_6$-$C_{10}$ alketh (1-5) sulfate as the principal detergent was more effective than the dodecyl sulfate or dodeceth (1-5) sulfate surfactant in removing a mono-$C_{12}$-$C_{18}$ alkyl quaternary ammonium conditioner from the hair—a soil unlike the soils which are typically removed by liquid dishwashing compositions.

SUMMARY OF THE INVENTION

As indicated above, the present invention primarily resides in the discovery that hair cleaning compositions containing a $C_6$-$C_{10}$ alketh (1-5) sulfate salt as the principal detergent, said sulfate being prepared by sulfating and neutralizing the condensation product of a $C_6$-$C_{10}$ alkanol with an average of one to five moles of ethylene oxide and also being at least 75% by weight of the anionic detergents present, are effective in removing a mono-$C_{12}$-$C_{18}$ alkyl quaternary ammonium conditioner from the hair. Thus, the invention relates to a method of removing the mono-alkyl quaternary conditioner from the hair and to the hair cleaning compositions for use in the inventive method. The invention also relates to a method of removing complexes previously formed on the hair between lauryl sulfate and/or laureth (1-5) sulfate anions and mono-$C_{12}$-$C_{18}$ alkyl quaternary ammonium cations.

Broadly, the present invention relates to a method of removing a mono $C_{12}$-$C_{18}$ alkyl quaternary ammonium hair conditioner from the hair having said conditioner thereon comprising the steps of (a) washing said hair having said conditioner thereon with an effective amount of a hair cleaning composition containing a water-soluble, $C_6$-$C_{10}$ alketh (1-5) sulfate salt as the principal detergent, said sulfate being prepared by sulfating and neutralizing the condensation product of a $C_6$-$C_{10}$ alkanol with an average of one to five moles of ethylene oxide and being at least 75% by weight of the total weight of anionic detergents present; and (b) rinsing the washed hair with water to remove said hair cleaning composition.

In a preferred aspect, the method comprises a repetition of steps a and b using a hair cleaning composition wherein the principal alketh (1-5) sulfate salt contains 8 to 10 carbon atoms in the alkyl group and contains less than 17% by weight of decyl monoethoxy sulfate salt. In its most preferred aspect, the hair cleaning composition will comprise 15% to 30% by weight of said alketh sulfate salt in an aqueous medium and said alkyl sulfate will be a mixture of a sulfated and neutralized condensation product of decyl alkanol with one mole of ethylene oxide and a sulfated and neutralized condensation product of decyl alkanol with three moles of ethylene oxide, said alkanols containing at least 80% by weight of $C_{10}$ alkyl groups.

Also within the scope of the invention is the hair cleaning composition for use in the inventive method which consists essentially of 5% to 50% by weight of a water-soluble $C_6$-$C_{10}$ alketh (1-5) sulfate salt as the principal detergent, said sulfate being prepared by sulfating and neutralizing the condensation product of a $C_6$-$C_{10}$ alkanol with an average of one to five moles of ethylene oxide and containing less than 17% by weight of decyl monoethoxy sulfate salt and being at least 75% by weight of the total weight of the anionic detergents present; and 50% to 95% by weight of a compatible, non-toxic, cosmetic vehicle.

In a preferred aspect, the hair cleaning composition will consist essentially of 8% to 40% by weight of a $C_8$-$C_{10}$ alketh (1-5) sulfate salt in an aqueous medium which contains in addition, an ingredient selected from the group consisting of 1% to 8% by weight of a zwitterionic detergent having the structural formula

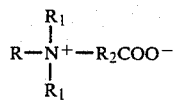

wherein R is $C_8$-$C_{18}$ alkyl or $C_8$-$C_{18}$ alkanamido $C_2$-$C_3$ alkyl, $R_1$ is $C_1$-$C_3$ alkyl and $R_2$ is a $C_1$-$C_4$ alkylene or hydroxyalkylene group, a $C_{12}$-$C_{15}$ alketh (1-5) sulfate salt or a $C_{10}$-$C_{18}$ olefin sulfonate salt, the proportion of said $C_{12}$-$C_{15}$ alketh (1-5) sulfate salt or said $C_{10}$-$C_{18}$ sulfonate salt being less than 25% by weight of the total anionic detergents present; 0.5% to 6% by weight of a $C_8$-$C_{18}$ alkanoic acid $C_2$-$C_3$ alkanolamide; and mixtures thereof.

DETAILED DESCRIPTION OF THE INVENTION

The principal detergent ingredient used in the inventive method and the inventive hair cleaning composition employed in said method is the water soluble salt of a sulfuric acid half ester of the condensation product of one mole of a $C_6$-$C_{10}$ alkanol with from one to five moles of ethylene oxide. These detergents are described in this specification as water-soluble $C_6$-$C_{10}$ alketh (1-5) sulfates or sulfate salts. Usually, the salt forming cation will be selected from the group consisting of sodium, potassium, ammonium and mono-, di- and triethanolammonium.

The methods of making the foregoing $C_6$-$C_{10}$ alketh (1-5) sulfate salts are well known and described in issued patents. Said sulfate salts are prepared by selecting an appropriate alkanol having a chain length of six to ten carbons, preferably eight to ten carbon atoms and most preferably ten carbon atoms, for reaction with ethylene oxide, i.e., for ethoxylation. These alkanols are generally manufactured synthetically although the $C_8$ and $C_{10}$ alkanols may be obtained by fractionating natural oils such as coconut or palm kernel oils. The $C_6$, $C_8$ and $C_{10}$ essentially unbranched alkanols can be obtained by hydrolyzing the aluminum alkoxides resulting from the reaction of ethylene and lower alkyl aluminum compounds as described in U.S. Pat. No. 3,415,861, the disclosure of which is incorporated by reference herein. On the other hand branched chain $C_6$-$C_{10}$ alkanols can be prepared by the "OXO" process. While both the unbranched and branched chained alkanols may be employed, substantially unbranched alkanols are preferred because the branched alkanols tend to be less biodegradable than the essentially linear alkanols. Thus, the weight percent of branched chain alkanols employed generally will be less than 20%, preferably less than 5%, by weight of the alkanols reacted with ethylene oxide.

The ethoxylation of the above-described alkanols generally will be done either by the method described in British Pat. No. 757,937 or by the method described in U.S. Pat. No. 2,870,220, the disclosures of which are incorporated by reference herein. In the method described in the British patent, one mole of $C_6$-$C_{10}$ alkanol is reacted with one to five moles of gaseous ethylene oxide at a temperature of about 120° C. to 150° C. in the presence of a small amount of an alkaline catalyst, e.g., sodium hydroxide, potassium hydroxide, sodium methylate, etc. In this method, the molar distribution of ethoxy groups per mole of alkanol is fairly broad. For example, the molar distribution obtained from the sulfated and neutralized, base catalyzed, reaction product of one mole of $C_{10}$ alkanol (more than 90% by weight of $C_{10}$) with one mole of ethylene oxide yields, by weight, about 40% of sodium decyl sulfate, 21% of decyl monoethoxy sulfate, 10% of decyl diethoxy sulfate, 10% of decyl triethoxy sulfate, 6% of decyl tetraethoxy sulfate, 4% of decyl pentaethoxy sulfate and 7% of decyl hexa or higher ethoxy sulfate. When two moles of ethylene oxide are reacted with one mole of said decanol the following distribution by weight results after sulfation and neutralization of the reaction product, for example:

8% decyl sulfate, 9% decyl monoethoxy sulfate, 9% of decyl diethoxy sulfate, 12% of decyl triethoxy sulfate, 12% of decyl tetraethoxy sulfate, 10% of decyl pentaethoxy sulfate, 9–10% of decyl hexaethoxy sulfate, 8% of sodium decyl heptaethoxy sulfate, 7% of sodium decyl octaethoxy sulfate, 5% of sodium decyl nonaethoxy sulfate, 4% of sodium decyl decaethoxy sulfate and about 7% of sodium decyl polyethoxy sulfates having eleven or more ethoxy groups. The reason for the broad distribution is that after one mole of ethylene oxide has reacted with the starting alkanol to form an ethoxylated alkanol, the next mole of ethylene oxide is as likely to react with the resultant ethoxylated alkanol as with the starting alkanol.

A second method of manufacturing an ethoxylated alkanol is described in U.S. Pat. No. 2,870,220. In the described method, primary and secondary $C_{10}$–$C_{18}$ alkanols are reacted with ethylene oxide in the presence of an acidic catalyst, e.g., chlorides or fluorides of aluminum, boron, iron, tin and titanium or sulfuric acid or phosphoric acid. This method results in high yields of monoethoxylated alkanols.

For sebaceous soil removal it is preferred to control the proportion of $C_6$–$C_{10}$ alkyl monoethoxy sulfate salt such that its concentration is less than about 17% by weight, the method described in British Pat. No. 757,937 is preferred. Thus, when the method of U.S. Pat. No. 2,870,220 is employed, it will be preferred to blend the essentially monoethoxylated alkanol from said method with the broad mixture of ethoxylated alkanols obtained using the method of British No. 757,937 or with higher ethoxylated material. Also, it is recognized that the broader distribution of alkanol ethoxylates can result in as much as 40% by weight of an alkyl sulfate salt that does not contain any ethylene oxide when, for example, one mole of alkanol is condensed with one mole of ethylene oxide. While such proportion of non-ethoxylated alkyl sulfate might be expected to be inefficient in removing the mono-$C_{12}$–$C_{18}$ alkyl quaternary ammonium conditioner based upon the teachings of U.S. Pat. No. 4,024,078, for example, surprisingly little decrease in efficiency is noted.

Sulfation of the $C_6$–$C_{10}$ alkyl ethoxylates is well known and the sulfating agents include oleum, sulfuric acid, chlorosulfonic acid and either gaseous or liquid sulfur trioxide. A preferred sulfation process comprises reacting a falling film of ethoxylated alkanol with a gaseous mixture of sulfur trioxide and air.

Neutralization of the alketh (1–5) sulfuric acids obtained by the sulfation process also is well known. Suitable neutralizing agents include sodium, potassium or ammonium hydroxide and mono-, di- or triethanolamine. Preferred neutralizing agents are sodium hydroxide, ammonium hydroxide and triethanolamine.

As stated above, the suitable alkyl ethoxy sulfate salts which are employed in this invention are $C_6$–$C_{10}$ alketh (1–5) sulfate salts. The number of ethoxy groups in the molecule is based upon the average number of moles of ethylene oxide in the range of one to five that is reacted with one mole of alkanol. In addition, the preferred salts are characterized by a weight concentration of decyl monoethoxy sulfate salt of about 17% or less. Further, the preferred alketh (1–5) sulfate salts will contain 8 to 10 carbon atoms in the alkyl group and most preferably the alkyl group will contain at least 80% or 90% by weight of decyl alkyl groups.

Generally, the hair cleaning compositions of this invention will contain about 5% to 50% by weight of the $C_6$–$C_{10}$ alketh (1–5) sulfate salt and said salt will be at least 75% by weight of the total weight of anionic detergent present. In preferred hair cleaning compositions, the proportion of the $C_6$–$C_{10}$ alketh (1–5) sulfate detergent will be from 8% to 40% by weight, with the proportion being 15% to 30% by weight in the most preferred compositions. To the extent that a hair cleaning composition contains only anionic $C_6$–$C_{18}$ alketh (0–12) sulfate detergent salts, the essential $C_6$–$C_{10}$ alketh (1–5) sulfate salts will constitute at least 75% by weight of the total anionic alkyl and alkyl ethoxy sulfate detergents present. When an anionic detergent is employed in combination with the principal $C_6$–$C_{10}$ alketh (1–5) sulfate salt, the proportion of the total anionic detergents will be the same as the proportions specified for such principal detergent, namely, 5%–50%, 8%–40% and 15%–30% respectively.

The other essential ingredient in the inventive hair cleaning compositions can be defined as compatible, non-toxic, cosmetic vehicle. The vehicle will vary according to the physical form of the hair cleaning composition. For example, sodium sulfate may be used as the vehicle in a hair cleaning powder. In liquid, paste and gel hair cleaning compositions, the vehicle usually will be an aqueous medium with water as the major component and in the liquid shampoos possibly minor proportions of a $C_2$–$C_3$ alcohol such as ethanol, isopropanol, glycerine, and propylene glycol will be present as a solubilizer. A $C_1$–$C_3$ alkyl substituted benzene sulfonate hydrotrope may be substituted for all or part of the alcohol solubilizer. Usually, the solubilizer will be less than 20%, preferably less than 10%, by weight of the aqueous medium when it is employed as the compatible vehicle.

In hair cleaning compositions containing only the essential detergent and vehicle components, the proportion of vehicle generally will be 50% to 95%, preferably 60% to 92% and most preferably 70% to 85%, by weight of said composition. While hair cleaning compositions containing only $C_6$–$C_{10}$ alketh (1–5) sulfate detergent and a compatible vehicle are satisfactory, preferred compositions will contain additional detergents such as $C_{12}$–$C_{18}$ alketh (1–5) sulfates, $C_{10}$–$C_{18}$ olefin sulfonates, zwitterionic betaine surfactants and alkanoic acid, mono- or di- ethanolamides to supplement the principal $C_6$–$C_{10}$ alketh (1–5)sulfate detergent.

A desirable detergent which may be added to the hair cleaning composition is a $C_{10}$–$C_{18}$ alketh (0–12) sulfate salt or mixture thereof. Preferably, the added sulfate salt will contain at least 65% by weight of $C_{12}$–$C_{15}$ alkyl groups and will have an average number of ethoxy groups of from one to five. As with the principal detergent, the sulfate salt is selected from the group consisting of sodium, potassium, ammonium and mono-, di- and triethanolammonium salts. Such added sulfate detergents enhance the oily soil removal properties and foaming properties of the resultant hair cleaning compositions. On the other hand where the added alketh (0–12) sulfate contains an average of 6 to 12 ethoxy groups in the molecule, the resultant hair cleaning composition is mildarand less irritating to the skin, but exhibits reduced foaming properties. However, as stated heretofore, the proportion of such added anionic sulfate detergent will not exceed 25% by weight of the total anionic detergents present in the resultant hair cleaning composition.

Another anionic detergent which desirably may be included in the hair cleaning compositions is a $C_{10}$–$C_{18}$ olefin sulfonate salt selected from the group consisting of sodium, potassium, ammonium and mono-, di- and triethanolammonium salts. Such detergents are obtained by sulfonating the appropriate olefin. Preferred olefin sulfonates contain 14–16 carbon atoms in the alkenyl group and are obtained by sulfonating an α-olefin of said chain length and neutralizing the reaction product. These anionic detergents enhance the foaming and cleaning properties of the principal detergent ingredient when present in the hair cleaning compositions in an amount which does not exceed 25% by weight of the total anionic detergent present therein.

Another detergent ingredient which can be included in the hair cleaning compositions of this invention is a zwitterionic betaine detergent having the following structural formula:

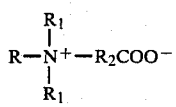

wherein R is $C_8$–$C_{18}$ alkyl or $C_8$–$C_{18}$ alkanamido $C_2$–$C_3$ alkyl, $R_1$ is $C_1$–$C_3$ alkyl and R is a $C_1$–$C_4$ alkylene or hydroxyalkylene group. These zwitterionic detergents may be described as a derivative of an aliphatic quaternary ammonium compound containing a $C_8$–$C_{18}$ branched-or straight-chain radical and containing an anionic group. Preferred zwitterionic betaine detergents are lauryl dimethyl ammonio acetate, lauryl myristyl dimethyl ammonio acetate, $C_8$–$C_{18}$ alkanamidopropyl dimethyl ammonio acetate and $C_8$–$C_{18}$ alkyl dimethyl ammonio acetate, with the $C_8$–$C_{18}$ alkanamidopropyl dimethyl ammonio acetate being most preferred.

In the inventive hair cleaning products, the zwitterionic detergent acts as a cleansing agent, a foam booster and a mildness agent. Generally, the proportion of zwitterionic detergent will range from 0.5% to 8%, preferably 1% to 5%, by weight. Also, when mildness to skin is an important consideration, the proportion of zwitterionic will be integrated with the proportion of the principal detergent and, desirably, the weight ratio of zwitterionic betaine detergent to principal detergent will be from about 1:100 to 2:1, preferably from 1:40 to 5:8.

In hair cleaning compositions particularly adapted for washing or cleaning hair which has been permanent waved or color treated, a $C_8$–$C_{18}$ alkanol may be substituted for part of the zwitterionic betaine detergent. In such compositions, the weight ratio of betaine to alkanol will be in the range of 3:1 to 1:2. Preferred alkanols are $C_{10}$–$C_{14}$ alkanols, with dodecanol being particularly preferred.

A further useful component in some of the inventive hair cleaning compositions is a $C_8$–$C_{18}$ alkanoic acid $C_2$–$C_3$ alkanolamide. This component is widely recognized as a foam builder and satisfactory alkanoic acid alkanolamides are lauric monoethanolamide, myristic monoethanolamide, lauric diethanolamide, myristic diethanolamide, lauric isopropanolamiieand coconut ($C_8C_{18}$) monoethanolamide. Preferred alkanoic acid alkanolamides contain 12 to 14 carbons in the acyl group. A particularly preferred compound is lauricmyristic monoethanolamide. Usually, the amount of alkanoic acid alkanolamide in the shampoo composition will be 0.5% to 6%, preferably 1% to 5%, by weight.

In some hair cleaning compositions both the zwitterionic betaine detergent and the alkanoic acid alkanolamide will be present for special reasons. In such compositions, the proportions of the two components may be controlled with respect to one another such that the weight ratio of betaine detergent to alkanoic acid alkanolamide is in the range of 1:4 to 4:1.

The described hair cleaning compositions are essentially unbuilt detergents, i.e., do not contain proportions of organic or inorganic builder salt in detergent building proportions. Thus, these inventive compositions can contain any of the usual adjuvants found in shampoo compositions provided that they do not interfere with the performance properties of the inventive hair cleaning compositions. Such additional ingredients include minor proportions of perfumes and colors for aesthetic purposes; opacifiers, such as ethylene glycol distearate or polystyrene; thickening agents such as gums or hydroxypropyl methyl cellulose or sodium chloride; sequestering agents such as citric acid, citrate or ethylenediamine tetraacetate; preservatives such as formaldehye or Dowicil ® 200 or monomethyloldimethyl hydantoin; fluorescent agents or optical whiteners; and magnesium sulfate. The total concentration of added ingredients usually will be less than 8%, preferably less than 5%, by weight of the total composition. These hair cleaning compositions are prepared by admixing the individual detergent ingredients. For example, hair cleaning compositions in powder form can be prepared by mixing the essential detergent in particulate form with a compatible vehicle in particulate form such as sodium sulfate. Alternatively, an aqueous mixture of the detergent and sodium sulfate may be spray dried to form a particulate hair cleaning composition. In preparing liquid compositions, the essential $C_6$–$C_{10}$ alketh (1–5) sulfate detergent is admixed with a compatible liquid vehicle such as water with agitation at a temperature in the range of about 32° C. to 65° C. Usually the individual detergents are added in the form of aqueous solutions or dispersions. When present, the alkanoic acid alkanolamide typically is added in liquid form as one of the last ingredients at a temperature below about 55° C. Additionally, it is desirable to add any solubilizing agent to the formula weight of water prior to the addition of the essential detergent ingredients in order to avoid formation of gels. Any additional ingredients, such as color and perfume usually are added with agitation after the other ingredients while cooling the mixture to a 25° C. to 32° C. temperature. The pH is usually adjusted, if necessary, to a pH in the range of 5–9, preferably 6.5–8.0, by addition of, for example, either sulfuric acid or citric acid or sodium hydroxide, potassium hydroxide or triethanolamine. Further, any adjustment of viscosity of liquid compositions may be achieved by including appropriate amounts of the appropriate solubilizers or thickening agents in the composition with such ingredients usually being added to the water at the beginning of the manufacturing cycle.

Usually, the viscosity of the liquid shampoos will be variable over the range of about 100 centipoises (cps) to 8000 cps., and preferably from 500 cps. to 5000 cps. Viscosity is measured using a Brookfield Digital Viscometer, Model RVT, with a #4 spindle rotating at 20 or 100 r.p.m. The rost preferred viscosity range is 600 cps. to 3000 cps. based upon current consumer preferences. However, it will be recognized by one skilled in the art that liquids of even higher viscosity can be achieved by including up to 4% by weight of a known thickening agent in the inventive compositions.

As mentioned heretofore, the inventive hair cleaning compositions are particularly effective in removing mono-$C_{12}$–$C_{18}$ alkyl quaternary ammonium hair conditioners from the hair, even when said conditioner is present on the hair in the form of a complex formed by the prior interaction of the cationic mono-$C_{12}$–$C_{18}$ alkyl quaternary ammonium ions and the anionic lauryl sulfate or lauryl ethoxy sulfate ions usually employed in prior art shampoos. It is recognized that said mono-alkyl quaternary conditioners are commonly employed in hair conditioning products and that said conditioners are deposited on the hair. While the deposited conditioner improves the wet and dry combing characteristics of hair treated therewith, the resultant deposit also reduces hair shine. It has been noted that the mono-alkyl quaternary conditioners are not removed completely from the hair by shampoos containing $C_{12}$ alkyl sulfate or $C_{12}$ alkyl ethoxy sulfate or mixtures thereof. Further, it has been discussed that these same shampoos do not completely remove any preformed water-insoluble complex of said mono-alkyl quaternary ammonium cation and the alkyl or alkyl ethoxy sulfate anion. Thus, the claimed hair cleaning compositions are effective in removing the dulling mono-$C_{12}$–$C_{18}$ quaternary conditioners—in uncomplexed or complexed form—from the hair. Furthermore, in removing said conditioners which are present in the form of an anionic-cationic complex, damage to the hair caused by complex induced scaling is reduced.

Surprisingly, the inventive method comprising the steps of (a) cleaning hair having a $C_{12}$–$C_{18}$ mono-alkyl quaternary conditioner thereon with an effective amount of a shampoo composition containing a water-soluble, $C_6$–$C_{10}$ alketh (1–5) sulfate salt as the principal detergent, said sulfate being prepared by sulfating and neutralizing the condensation product of a $C_6$–$C_{10}$ alkanol with an average of one to five moles of ethylene oxide and being at least 75% by weight of the total weight of anionic detergent present, and (b) rinsing the cleansed hair with water to remove said cleaning composition is effective in removing the dulling deposit of said quaternary conditioner from the hair.

In the preferred method, steps (a) and (b) are repeated a second time and the principal surfactant is present in an amount of 8% to 40% by weight of the shampoo which most preferably is a mixture of a sulfated and neutralized condensation product of decyl alkanol with one mole of ethylene oxide and a sulfated and neutralized condensation product of decyl alkanol with three moles of ethylene oxide, said alkanol containing at least 80% by weight of $C_{10}$ alkyl groups.

In the inventive method, the temperature of the water which is used to wet the hair usually is from 29° C. to 43° C., preferably from 35° C. to 41° C. The temperature of the water employed to rinse the cleaning composition from the hair usually is about 35° C. to 41° C. In the described method, the cleaning composition generally is applied to the hair in liquid form, e.g., directly from the container of liquid cleaning composition or after mixing a powdered shampoo with water to form a 5% to 50% aqueous cleaning composition. Compositions in liquid form may be applied directly to the hair and scalp or may be placed in the hand of the user for application to the hair and scalp. If desired, the composition placed in the hands may be worked into a lather before being applied to the hair. However, in all cases, the cleaning composition will be worked into the hair and saclp by the user's fingers for a period of from about one to five minutes in order to distribute the composition through the hair before being rinsed from the hair.

The results in Tables A–D below confirm that the commonly used stearalkonium chloride (stearyl dimethylbenzyl ammonium chloride) conditioner is not completely removed from the hair by the various anionic detergents used in shampoo compositions. Furthermore, the results in the table confirm the efficiency of the inventive $C_6$–$C_{10}$ alketh (1–5) sulfate salts in removing said conditioner.

Tables A–D set forth shine values for hairs that have been treated with a stearalkonium chloride conditioner and then washed with a shampoo composition comprising 20% by weight of a specific anionic surfactant. In these tests, tresses of virgin oriental hair having a length of about ten inches and a weight of about three grams are prewashed twice with 5 ml. of 20% by weight of sodium n-$C_8$–$C_{10}$ (45/55) alketh (1) sulfate in water, rinsed for one minute under flowing 38° C. water and air dried. Each air dried tress is wetted with water, treated with two milliliters of a dispersion of 1% by weight of stearalkonium chloride in water by working said composition into the tress with the fingers for one minute and then rinsing for one minute under flowing water at 38° C. After drying, the resultant tress may be called a conditioned tress. The wet tress having conditioner thereon is then treated with 0.5 ml of a shampoo consisting of 20% by weight of the test anionic detergent in water by working said aqueous shampoo into the tress for one minute with the fingers thereby generating a foam and rinsing the tress under flowing 38° C. water for one minute. After drying, the resultant tress may be called a shampooed tress. The values in Table A are based upon tresses which have dried after three alternating treatments of conditioner and anionic detergent shampoo.

The shine values in Tables A–D are based upon values obtained using a Murakami GP-1R automatic goniophotometer. With this instrument shine or luster is based upon a measure of scattered light intensity as a function of angle, with shine increasing with increasing specular reflection and decreasing with increasing diffuse scattering. In the test, a single hair fiber is held taut and irradiated with light at an angle of 30°, with all angles being measured with respect to the perpendicular to the fiber at 0° and the scattered light being measured by rotating a photomultiplier tube from 0° to 75°. Shine or luster is determined from the following equation:

$$L = S/DW(\tfrac{1}{2}) \qquad (1)$$

wherein L equals luster, S is the integrated specular reflectance which is obtained by measuring the area of the specular peak, D is the integrated diffuse reflectance which is obtained by connecting the scattered light intensities at 0° and 75° and measuring the area under the resulting line, and $W(\tfrac{1}{2})$ is the width of the specular peak at half-height. L is measured for twenty-one hairs taken from three test tresses (63 readings total). These readings are then averaged to obtain a single shine value. In practice, the shine value obtained by the equation correlates well with shine results obtained from subjective evaluations by skilled evaluators.

TABLE A

| Anionic Detergent[a] | Shine |
|---|---|
| Sodium hexeth (1) sulfate | 1.794 |

TABLE A-continued

| Anionic Detergent[a] | Shine |
|---|---|
| Sodium hexeth (3) sulfate | 1.431 |
| Sodium hexeth (5) sulfate | 1.505 |
| Sodium $C_8$-$C_{10}$ (45/55) alketh (1) sulfate | 1.517 |
| Triethanolammonium lauryl sulfate (TEALS) | 0.676 |
| Sodium $C_6$-$C_{10}$ (45/55) alketh (1) sulfate control A[b] | 1.567 |

[a] With the exception of TEALS, the anionic detergent is the sodium salt of the sulfuric acid of the base-catalyzed reaction product of one mole of described alkanol with one, three or five moles of ethylene oxide.
[b] Control A is the sodium salt of the sulfated adduct of the reaction product of $C_8$-$C_{10}$ alkanol (45% by weight of $C_8$ alkyl groups and 55% by weight of $C_{10}$ alkyl groups) with one mole of ethylene oxide and the hair tresses only are washed three times with this detergent, i.e., no conditioner is applied to the tress.

TABLE B

| Anionic Detergent[a] | Shine |
|---|---|
| Sodium octeth (1) sulfate[c] | 1.569 |
| Sodium octeth (3) sulfate | 1.609 |
| Sodium octeth (5) sulfate | 1.680 |
| Sodium $C_8$-$C_{10}$ (45/55) alketh (1) sulfate | 1.356 |
| Sodium $C_8$-$C_{10}$ (45/55) alketh (1) sulfate control A | 1.840 |

[c] $C_8$ alkanol contained ≧ 90% by weight of $C_8$ alkyls.

TABLE C

| Anionic Detergent[a] | Shine |
|---|---|
| Sodium deceth (1) sulfate[d] | 1.576 |
| Sodium deceth (3) sulfate | 1.662 |
| Sodium deceth (5) sulfate | 1.524 |
| Sodium $C_8$-$C_{10}$ (45/55) alketh (1) sulfate | 1.574 |
| Sodium $C_8$-$C_{10}$ (45/55) alketh (1) sulfate control A[b] | 1.673 |

[d] $C_{10}$ alkanol contained ≧ 90% by weight of $C_{10}$ alkyls.

TABLE D

| Anionic Detergent[a] | Shine |
|---|---|
| Sodium dodeceth (1) sulfate[e] | 0.876 |
| Sodium dodeceth (2) sulfate | 1.048 |
| Sodium dodeceth (3) sulfate | 0.882 |
| Sodium dodeceth (5) sulfate | 0.910 |
| Sodium $C_8$-$C_{10}$ (45/55) alketh (1) sulfate | 1.427 |
| Sodium $C_8$-$C_{10}$ (45/55) alketh (1) sulfate control A[b] | 1.732 |

[e] $C_{12}$ alkanol contained ≧ 90% by weight of $C_{12}$ alkyls.

The results in Table D above clearly demonstrate the heretofore described problem namely, commonly used sodium dodeceth (1-5) sulfate detergents do not completely remove cationic stearalkonium chloride conditioner from the hair. More specifically, the shine value obtained using only sodium $C_8$-$C_{10}$ alketh (1) sulfate detergent, namely 1.732, is much greater than the shine values for the tresses treated with the conditioner and cleaned with sodium dodeceth (1-5) sulfate anionic detergent. Differences in shine values in Tables A-D are due to the presence of deposits of mono $C_{12}$-$C_{18}$ alkyl quaternary conditioner on the surface of the hair after it is washed with the cleaning composition. Tables A-C confirm that sodium $C_6$-$C_{10}$ alketh (1-5) sulfates are effective detergents in removing stearalkonium chloride from the hair. This fact is evident from a comparison of said shine values with the shine values obtained when a tress is subjected to cleaning only—no conditioner treatment at all—using the control A shampoo containing sodium $C_8$-$C_{10}$ (45/55) alketh (1) sulfate. The latter tress is deemed to be a clean tress and thus the individual hairs from said tress represent clean hair which is free of mono-$C_{12}$-$C_{18}$ quaternary conditioner.

The instrumental evaluation of shine based upon readings obtained using individual hairs closely agrees with subjective evaluation of the hairs in the form of tresses. Subjective evaluations of hair tresses are performed using groups of six tresses receiving different experimental treatments. Each tress is clamped at the root end onto a frame, wrapped over a 35 millimeter cylinder mounted on the frame, and, finally, clamped down at the tip end. This setup insures that the tresses are all oriented in the same manner towards the viewing light and tends to minimize orientation differences among the individual hairs comprising the tresses. Tresses are viewed under two lamps, each of which holds two cylindrical 60 watt tungsten bulbs. These bulbs are aligned end to end in a single row approximately ten incheses above the tresses. This configuration maximizes the chance that each tress is receiving an equal amount of light. After mounting, tresses are evaluated by at least sixteen panelists, each of whom is asked to rank the tresses in order of relative shine. After one evaluation, the positions of the tresses are interchanged and the rankings repeated in order to minimize any positional biases. The data from the above rankings are evaluated statistically.

The low shine values listed in Table D for tresses treated with conditioner and then washed with sodium lauryl (dodecyl) sulfate or sodium laureth (1-5) sulfate clearly indicate that a deposit is left on the hair after cleaning with these surfactants. The nature of the deposit is defined by experiments in which hair tresses and wool swatches were treated with mono-$C_{12}$-$C_{18}$ alkyl quaternary ammonium conditioner, cleaned with lauryl sulfate and/or laureth (3) sulfate and then treated with red dye and rinsed under running tap water. The dye was observed to be easily rinsed from the hair or wool surface. Red dye 80 is an anionic dye and is well known to rinse from hair or wool unless a cationic species such as mono-$C_{12}$-$C_{18}$ alkyl quaternary ammonium conditioner is previously adsorbed to the hair or wool surface. In this case red dye 80 binds to the cationic species and cannot be removed from the hair or wool by rinsing with water. Since in the above mentioned experiments, the dye was removed, one can conclude that the cationic mono-$C_{12}$-$C_{18}$ alkyl quaternary ammonium conditioner was either removed from the hair and wool surfaces by shampooing or else formed a complex with the anionic surfactant, thus rendering it unavailable for binding to the dye. The data in Table D indicate the presence of a significant amount of deposit under the conditions employed in the dyeing experiments. Thus, the conditioner was not removed in these experiments, clearly indicating that treating hair with mono-$C_{12}$-$C_{18}$ alkyl quaternary ammonium conditioner and then cleaning with lauryl sulfate or laureth (3) sulfate leads to formation on the hair surface of an insoluble complex between said conditioner and the anionic surfactant which results in a reduced shine value.

In addition to correlating well with tress evaluations, shine measurements correlate well with the shine perceived by skilled human evaluators in half head tests wherein the hair of volunteers conditioned with stearalkonium chloride is cleaned with the test cleaning compositions. In half head tests, the test cleaning composition is used to cleanse one half of the head and a control or cleaning composition is employed on the other half of the head.

Half head tests are performed by parting a panelist's hair in the center, subjecting each side to a treatment with a hair cleaning composition followed by a water rinse to prewash the hair and thereafter subjecting each side to three cycles of alternate treatments of conditioner and cleaning composition-conditioner/cleaning composition prior to the removal of 30-40 hairs which are employed in obtaining an instrumental shine value. In each hair cleaning treatment, each half of the head is cleansed by the operator with 5 milliliters (ml.) of a hair cleaning composition consisting of 20% by weight of anionic detergent in water by working the aqueous shampoo into the wetted hair with the fingers to generate a foam for one minute and rinsing the cleaned hair for one minute under running tap water at 38° C. One half of the head is washed with the test hair cleaning composition and the other half of the head is washed with a control hair cleaning composition, e.g., a triethanolammonium lauryl sulfate containing cleaning composition. In each conditioner treatment, fifteen grams of a conditioning composition consisting of either 6% by weight of stearalkonium chloride in aqueous ethanol (30% by weight of ethanol and 70% by weight of water) or a commercial conditioner sold under the name White Rain ® is worked into each side of the head by the operator for one minute followed by a rinse for one minute under flowing tap water at 38° C. Each conditioner treatment is followed by a cleaning treatment and these two treatments are referred to as a conditioner/hair cleaner cycle. In the half head tests, said conditioner/hair cleaner cycle is repeated three times to simulate what happens upon continued usage. In all cases, each half head is prewashed with two applications of hair cleaning composition, each followed by a rinse, prior to the initiation of the test cycles.

After three conditioner-hair cleaner cycles, 30-40 hairs are removed from each half of the head and are employed in obtaining an instrumental shine value. Subjective compositions of both sides of the head are made by viewing in a darkened room under an overhead point source 500 watt bulb by four to six skilled evaluators.

Tables E and F set forth half headtest results using stearalkonium chloride (SAC) hair conditioner and the commercial conditioner (White Rain) wherein one half the head is cleaned with a cleaner containing triethanolammonium lauryl sulfate (TEALS) anionic detergent and the other half of the head is cleaned with the control A shampoo—n-$C_8$-$C_{10}$ alketh (1) sulfate anionic detergent. In Tables E and F, a positive value in the column entitled "Subjective Shine" shows a shine advantage for the control A shampoo composition of this invention. Furthermore, the column "Delta Shine" sets forth the difference in shine measured using 30 to 40 hairs taken from the side of the head washed with the inventive shampoo as compared with TEALS shampoo using the Murakami GP-1R goniophotometer technique discussed above. These results show that the inventive method of cleaning the hair having conditioner thereon with a hair cleaning composition containing the inventive $C_6$-$C_{10}$ alketh (1-5) sulfate salt consistently results in hair having higher shine, thereby confirming significantly improved removal of the SAC conditioner therefrom. These results also show that this shine advantage is observed for both virgin hair (tests nos. 3, 4, 5 and 6) and for damaged hair (tests nos. 7-13), e.g., hair which has been subject to permanent waving or bleaching, with the difference in shine being greatest on damaged hair.

TABLE E

| | SAC Conditioner | |
|---|---|---|
| Test Nos. | Subjective Shine | Delta Shine[1] |
| 3 | + | 0.26 |
| 4 | + | 0.12 |
| 5 | + | 0.11 |
| 6 | + | 0.38 |
| 7 | + | 0.50 |
| 8 | − | 0.44 |
| 10 | + | 0.80 |
| 11 | + | 0.38 |
| 12 | + | 0.63 |
| 13 | + | 0.80 |

[1]Measured at 30° incidence angle in Table E.

TABLE F

| | Commercial Conditioner | |
|---|---|---|
| Test Nos. | Subjective Shine | Delta Shine[2] |
| 15 | + | 0.74 |
| 18 | + | 0.37 |
| 19 | + | 0.15 |
| 21* | + | 0.55 |

*Cleaned with Example 1 cleaning composition.
[2]Measured at 45° incidence angle.

The negative subjective shine value for Test No. 8 is an anomaly which is believed to be due to the fact that the subject had curly hair and the hair on the TEALS side was more dniformly aligned due to the imcomplete removal of the monoalkyl quaternary conditioner. Sometimes, curly hair is characterized by such a high degree of misalignment that an increase in alignment of the duller side of the head makes it appear to be shinier. The erroneous nature of the subject evaluation is supported by the instrumental delta shine values based upon analysis of individual hairs—a method wherein orientation of the hair is not a problem.

Three subjects having permanent waved hair were evaluated in the same manner as the foursubjects in Table F with the exception that the shine measurementswere made prior to the final cleaning step. Again, the subjects washed with the inventive shampoo A were favored subjectively as well as instrumentally, i.e., delta shine values of 0.50, 0.74 and 0.88. A fourth subject having curly hair evaluated in the same manner gave results similar to those noted in Test No. 8 in Table E. However, in all of these evaluations the absolute shine value was lower than the absolute shine value for hair subjected to the final cleaning step.

Specific inventive shampoo compositions are illustrated by the following examples. All quantities indicated in the examples or elsewhere in the specification are by weight unless otherwise indicated.

EXAMPLE 1

A preferred hair cleaning composition which is effective in removing cationic conditioner from the hair is set forth below:

| Ingredient | % by weight |
|---|---|
| Sodium deceth (1) sulfate[f] | 10% |
| Sodium deceth (3) sulfate[g] | 10% |
| $C_8$-$C_{18}$ alkylamidopropyl dimethyl betaine[h] | 4% |
| Polyethylene glycol (55) propylene glycol dioleate | 0.8% |
| Color, perfume, water | q.s. |

(f)Obtained from Vista Chemical Company under the tradename Alfonic 10-26 which contains, by weight, 39.5% of sodium decyl sulfate, 21.3% of sodium decyl monoethoxy sulfate, 12.2% of sodium decyl diethoxy sulfate, 9.8% of decyl triethoxy sulfate, 6.4% of sodium decyl tetraethoxy sulfate, 3.9% of sodium decyl pentaethoxy sulfate and 6.9% of sodium decyl polyethoxy sulfates having six or more ethoxy groups.

(g)Obtained from Vista Chemical Company under the tradename Alfonic 10-46 which contains, by weight 7.6% of sodium decyl sulfate, 9.4% of sodium decyl monoethoxy sulfate, 9.4% of sodium decyl diethoxy sulfate, 11.2% of sodium decyl triethoxy sulfate, 11.8% of sodium decyl tetraethoxy sulfate, 10.4% of sodium decyl pentaethoxy sulfate, 9.5% of sodium decyl hexaethoxy sulfate, 8.2% of sodium decyl heptaethoxy sulfate, 6.7% of sodium decyl octaethoxy sulfate, 5.2% of sodium decyl nonaethoxy sulfate, 3.9% of sodium decyl decethoxy sulfate and 6.7% of sodium decyl polyethoxy sulfates having eleven or more ethoxy groups.

(h)Purchased from Goldschmidt Chemical Corporation under the tradename Tego betaine L-7 which contains 30% by weight of the betaine in water.

EXAMPLE 2

Another preferred cleaning composition which is effective in removing cationic hair conditioner from oily hair follows:

| Ingredient | % by weight |
| --- | --- |
| Sodium deceth (1) sulfate(f) | 10% |
| Sodium deceth (3) sulfate(g) | 10% |
| Sodium $C_{12}$-$C_{14}$ alketh (2) sulfate(i) | 4% |
| Hydroxyethyl cellulose (Natrosol 250 HR) | 0.8% |
| Color, perfume, preservative, water | q.s. |
| | 100.0 |

(i)Purchased from Henkel under the tradename Standapol ES-2 as 27.6% (by weight) solution of the sodium alketh (2) in water.

EXAMPLE 3

A preferred hair cleaning composition which is mild and effective for removing hair conditioner from permanent waved and color treated hair follows:

| Ingredient | % by weight |
| --- | --- |
| Sodium deceth (1) sulfate(f) | 10% |
| Sodium deceth (3) sulfate(g) | 10% |
| $C_8$-$C_{18}$ alkanamido propyl dimethyl betaine(h) | 1% |
| Dodecanol | 1% |
| Polyethylene glycol (55) propylene glycol dioleate | 1.2% |
| Color, perfume, preservative and water | q.s. |
| | 100.0 |

The compositions of Examples 1–3 were evaluated by three panels consisting of twenty-five women in each panel—all of whom used styling aids, e.g., conditioners, mousses, hair sprays, etc. In each evaluation, the control cleaning composition was the test subject's favorite brand of shampoo. The results indicated that the compositions of Examples 1–3 were preferred for cleaning by each of the panels and that the composition of Example 3 was the overall preference of its panel.

EXAMPLE 4

The composition of Example 1 is repeated with the exception that the concentration of betaine is increased from 4% to 7.5% by weight and the concentration of water is decreased by 3.5%. This composition is compared with clean hair (Control A) and with hair cleansed with $C_8$-$C_{10}$ alketh (1) sulfate according to the procedure employed in Tables A-D and it exhibited shine values almost as great as clean hair, thereby indicating essentially complete removal of the SAC conditioner by this hair cleaning composition.

The invention has been described with respect to various examples and illustrations thereof but is not to be limited to these because it is clear that one of skill in the art, with the present description before him, will be able to utilize substitutes and equivalents without departing from the invention.

What is claimed is:

1. A method of removing a mono $C_{12}$-$C_{18}$ alkyl quaternary ammonium hair conditioner from the hair having said conditioner thereon comprising the steps of (a) cleaning said hair having said conditioner thereon with an effective amount of a hair cleaning composition containing a water-soluble, $C_6$-$C_{10}$ alketh (1-5) sulfate salt as the principal detergent, said sulfate being prepared by sulfating and neutralizing the condensation product of a $C_6$-$C_{10}$ alkanol with an average of one to five moles of ethylene oxide and being at least 75% by weight of the total weight of anionic detergents present; and (b) rinsing the cleansed hair with water to remove said hair cleaning composition.

2. A method according to claim 1 wherein said hair cleaning composition comprises 5% to 50% by weight of said $C_6$-$C_{10}$ alketh (1-5) sulfate salt in 50% to 95% by weight of a compatible, non-toxic cosmetic vehicle.

3. A method according to claim 2 wherein said hair cleaning composition comprises 8% to 40% by weight of said $C_6$-$C_{10}$ alketh (1-5) sulfate salt solubilized in said vehicle which is an aqueous medium which is primarily water.

4. A method according to claim 1 wherein said rinsing step is followed by a repetition of steps a and b.

5. A method according to claim 2 wherein said rinsing step is followed by a repetition of steps a and b.

6. A method according to claim 3 wherein said rinsing step is followed by a repetition of steps a and b.

7. A method according to claim 2 wherein said sulfate salt contains 8 to 10 carbon atoms in the alkyl group.

8. A method according to claim 7 wherein said alkyl group contains at least 80% by weight of decyl groups.

9. A method according to claim 8 wherein said alketh (1-5) sulfate salt is present in an amount of 15% to 30% by weight of said hair cleaning composition and is a mixture of a sulfated and neutralized condensation product of decyl alkanol with one mole of ethylene oxide and a sulfated and neutralized condensation product of decyl alkanol with three moles of ethylene oxide, said alkanol containing at least 80% by weight of $C_{10}$ alkyl groups.

10. A method according to claim 1 wherein said $C_6$-$C_{10}$ alketh (1-5) sulfate salt contains less than 17% by weight of decyl ether monoethenoxy sulfate salt and said condensation product is produced in the presence of a basic catalyst.

11. A method according to claim 10 wherein said hair cleaning composition comprises 5% to 50% by weight of said $C_6$-$C_{10}$ alketh (1-5) sulfate salt in an aqueous medium.

12. A method according to claim 11 wherein said hair cleaning composition comprises 8% to 40% by weight of said $C_6$-$C_{10}$ alketh (1-5) sulfate salt solubilized in an aqueous medium.

13. A method according to claim 10 wherein said rinsing step is followed by a repetition of steps a and b.

14. A method according to claim 11 wherein said rinsing step is followed by a repetition of steps a and b.

15. A method according to claim 12 wherein said rinsing step is followed by a repetition of steps a and b.

16. A method according to claim 11 wherein said sulfate salt contains 8 to 10 carbon atoms in the alkyl group.

17. A method according to claim 16 wherein said alkyl group contains at least 80% by weight of decyl groups.

18. A method according to claim 17 wherein said alketh (1–5) sulfate salt is present in an amount of 15% to 30% by weight of said shampoo and is a mixture of a sulfated and neutralized condensation product of decyl alkanol with one mole of ethylene oxide and a sulfated and neutralized condensation product of decyl alkanol with three moles of ethylene oxide, said alkanol containing at least 80% by weight of $C_{10}$ alkyl groups.

19. A hair cleaning composition for removing a mono $C_{12}$–$C_{18}$ alkyl quaternary ammonium conditioner from hair having said conditioner thereon which consists essentially of 5% to 50% by weight of a water-soluble $C_6$–$C_{10}$ alketh (1–5) sulfate salt as the principal detergent, said sulfate being prepared by sulfating and neutralizing the base-catalyzed, condensation product of a $C_6$–$C_{10}$ alkanol with an average of one to five moles of ethylene oxide and containing less than 17% by weight of decyl monoethoxy sulfate salt and being at least 75% by weight of the total weight of anionic detergent present; and 50% to 95% by weight of a compatible, nontoxic cosmetic vehicle.

20. A hair cleaning composition according to claim 19 wherein said vehicle is an aqueous medium which is primarily water.

21. A hair cleaning composition according to claim 20 wherein the proportion of said $C_6$–$C_{10}$ alketh (1–5) sulfate salt is 15% to 30% by weight of said shampoo and said salt is a mixture of a sulfated and neutralized condensation product of decyl alkanol with one mole of ethylene oxide and a sulfated and neutralized condensation product of decyl alkanol with three moles of ethylene oxide, said alkanol containing at least 80% by weight of $C_{10}$ alkyl groups.

22. A hair cleaning composition according to claim 21 which includes, in addition, from 0.5% to 8% by weight of a zwitterionic detergent having the structural formula

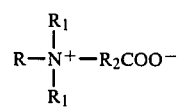

wherein R is $C_8$–$C_{18}$ alkyl or $C_8$–$C_{18}$ alkanamido $C_2$–$C_3$ alkyl, $R_1$ is $C_1$–$C_3$ alkyl and $R_2$ is a $C_1$–$C_4$ alkylene or hydroxyalkylene group.

23. A hair cleaning composition according to claim 22 which includes, in addition, from 0.5% to 4% by weight of a $C_8$–$C_{14}$ alkanol.

24. A hair cleaning composition according to claim 21 which includes, in addition, a $C_{12}$–$C_{15}$ alketh (1–5) sulfate salt, the proportion of said $C_{12}$–$C_{15}$ alketh (1–5) sulfate salt being less than 25% by weight of the total anionic detergents present.

25. A hair cleaning composition according to claim 21 which includes in addition, a $C_{10}$–$C_{18}$ olefin sulfonate salt, the proportion of said olefin sulfonate salt being less than 25% by weight of the total anionic detergents present.

* * * * *